(12) United States Patent
Rutter et al.

(10) Patent No.: US 9,301,491 B2
(45) Date of Patent: Apr. 5, 2016

(54) LOBLOLLY PINE TREE NAMED '01PM0038'

(71) Applicant: ArborGen Inc., Ridgeville, SC (US)

(72) Inventors: Mark Rutter, Ridgeville, SC (US); Alice Perry, Ridgeville, SC (US); Phil Dougherty, Ridgeville, SC (US); Jeff Wright, Ridgeville, SC (US); Richard Bryant, Ridgeville, SC (US); Patrick Cumbie, Ridgeville, SC (US)

(73) Assignee: ArborGen Inc., Ridgeville, SC (US)

( * ) Notice: Subject to any disclaimer, the term of this patent is extended or adjusted under 35 U.S.C. 154(b) by 375 days.

(21) Appl. No.: 13/800,338

(22) Filed: Mar. 13, 2013

(65) Prior Publication Data

US 2014/0283160 A1    Sep. 18, 2014

(51) Int. Cl.
*A01H 7/00* (2006.01)
*A01H 1/00* (2006.01)
*A01H 4/00* (2006.01)

(52) U.S. Cl.
CPC .. *A01H 7/00* (2013.01); *A01H 1/00* (2013.01); *A01H 4/00* (2013.01)

(58) Field of Classification Search
None
See application file for complete search history.

(56) References Cited

U.S. PATENT DOCUMENTS

2010/0058491 A1\* 3/2010 Surritte et al. ................ 800/260

\* cited by examiner

*Primary Examiner* — David H Kruse
(74) *Attorney, Agent, or Firm* — Foley & Lardner LLP (57) ABSTRACT

A new and distinct variety of loblolly pine tree named '01PM0038', particularly characterized by high rust resistance, uniform, rapid growth, stem straightness and moderate branch angle.

11 Claims, 4 Drawing Sheets

(4 of 4 Drawing Sheet(s) Filed in Color)

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cacgacgttg taaaacgac                                                      19

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagctctctt aatagcctcg ggcacatagc aacgctgaag a                              41

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcaaggaatt cattggagcc tttggccata tcaaacccat                                    40

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacattctag catgccccac ttgtggtgga tgtctctcct c                                  41

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccatgcatc aattcaagtt tgtgcgtgga tatggaaaaa                                    40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagaacatct gccttgagcc ctggcatgat gggtttctct                                    40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acttagtggg aaggggggaa ttcctcagcc aaaagctctc                                    40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcaaggggaa ttgcttatga gggatcgcat cagctgtaat                                    40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
caggtggctt ggatttcatt tcattcaagc gtcctgctta                              40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agggaaaccg cggattatag ccggaatgaa gattgcagtt                              40

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catgcatgtg tggaggagtc tcatgtgctt tgatcccct                               39

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acacatgtct tgaggagttc aatttgatct ataactttca cc                           42

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgctccctc agctcttcca gacgtcactg ccattaccc                               39
```

LOBLOLLY PINE TREE NAMED '01PM0038'

SEQUENCE LISTING

The instant application contains a Sequence Listing which has been submitted in ASCII format via EFS-Web and is hereby incorporated by reference in its entirety. Said ASCII copy, created on Mar. 22, 2013, is named 044463-1228_SL.txt and is 3,262 bytes in size.

FIELD OF THE INVENTION

The present invention relates to a new, distinct and stable variety of pine tree, botanically known as *Pinus taeda* L. of the Pinaceae family, commonly known as loblolly pine, and hereinafter referred to by the variety denomination '01PM0038'. The present invention relates to tissue cultures which are the loblolly pine '01PM0038', as well as, plants and plant parts, such as, pollen, seeds, cones, inflorescence, needles, embryos, cuttings, seedlings, bark, wood, oils, lumber or timber obtained from all of the morphological and physiological characteristics of loblolly pine '01PM0038'. The present invention further relates to harvested products obtained from loblolly pine '01PM0038', such as wood, oil, pulp or paper. The present invention also relates to methods for producing these tissue cultures, regenerating '01PM0038' plants therefrom, as well as, progeny of the loblolly pine '01PM0038'. The present invention relates to a method of producing loblolly pine, wherein the method is somatic embryogenesis comprising the tissue culture and regeneration of the loblolly pine '01PM0038' plants. The present invention further relates to making rooted cuttings of the reproduced '01PM0038' plants by planting the cuttings. The present invention also relates to a method of producing loblolly pine progeny or hybrids thereof, comprising the steps of (a) crossing loblolly pine '01PM0038', either as the female or seed parent or male or pollen parent, with a second pine variety, and (b) selecting progeny. The present invention also relates to a method of producing loblolly pine progeny or hybrid thereof, comprising the steps of (a) crossing loblolly pine '01PM0038', as either the female or seed parent or male or pollen parent, with a second pine variety, (b) harvesting seeds produced from said cross, and (c) producing and selecting progeny from said harvested seeds. Furthermore, the present invention relates to a method of producing loblolly pine progeny, comprising the steps of selfing loblolly pine '01PM0038', and (b) selecting progeny.

BACKGROUND OF THE INVENTION

The present invention relates to a new, distinct and stable variety of pine tree, botanically known as *Pinus taeda* of the Pinaceae family, commonly known as a loblolly pine, also known as Arkansas pine, North Carolina pine and oldfield pine, and hereinafter referred to by the variety denomination '01PM0038'.

Loblolly pine is native to the southeastern United States. Typical loblolly pine grows within a range of about 30 to 35 m in height and about 0.4 to 1.5 m in diameter. Needles of loblolly pine are arranged in bundles of three, which are sometimes twisted, and measure within a range of about 12 to 22 cm. Cones of loblolly pine are initially green in color, maturing to a pale brown, measure within a range of about 7 to 13 cm in length, and about 2 to 3 cm in width when closed, and maturing to about 4 to 6 cm in width once opened, and contain scales with a sharp spine about 3 to 6 mm in length. Loblolly pine has a vigorous growth rate and is grown for lumber and pulp fibers. Methods for reproduction and cultivation of loblolly pine are well known. For a detailed discussion, reference is made to the following publications, which are incorporated by reference: Becwar and Pullman, *IPST Technical Paper Series Number* 528, Institute of Paper Science and Technology (1994) pp. 1-18; Pullman and Johnson, *Ann. For. Sci.* 50 (2002) pp. 663-668; *Seeds of Woody Plants in the United States*, USDA Agricultural Handbook 450 (1974) pp. 608-631; Dorman, K. W., *The Genetics and Breeding of Southern Pines*, USDA Agricultural Handbook 471 (1976) pp. 24-51; Duryea and Dougherty, *Forest Regeneration Manual*, Kluwer Academic Publishers (1991) pp. 433.

Since loblolly pine is a commercially important forest species, research studies have been undertaken to identify promising loblolly pine varieties and hybrids which express a) resistance to problematic diseases and pests, such as fusiform rust and bark beetles, b) weather tolerance, such as extreme cold and drought tolerance c) stem strength and straightness, d) improved wood quality, and e) vigorous growth rate. Research studies have been conducted to identify such promising loblolly pine varieties and hybrids. In addition, the distinctive genetic fingerprint for these loblolly pine varieties can be analyzed. Numerous reproductive methods have been developed for loblolly pine varieties. In particular, asexual propagation by the method of somatic embryogenesis is described in U.S. Pat. No. 6,372,494 for conifers, and in U.S. patent application Ser. No. 11/245,267 for loblolly pine, which are hereby incorporated by reference in their entirety herein.

SUMMARY OF THE INVENTION

The present invention provides a new loblolly pine tree selection that possesses high rust resistance; uniform, rapid growth; stem straightness; and moderate branch angle.

These and other objectives have been achieved in accordance with the present invention which provides '01PM0038' as a new, distinct and stable variety of loblolly pine that is a product of a planned breeding program conducted by the inventor(s) in 2000 in Ravenel, S.C. The new loblolly pine '01PM0038' is a progeny of a first-generation selection pollinated by a second-generation selection. The female or seed parent is the unpatented *Pinus taeda* variety designated AG-373 selected in Williamsburg County, South Carolina, and is a first-generation selection. The male or pollen parent is the unpatented *Pinus taeda* variety designated AG-76 selected in a progeny test in Georgetown County, South Carolina, and is a second-generation selection.

OBJECTS OF THE INVENTION

The present invention relates to tissue cultures which produce the loblolly pine '01PM0038' and clones produced from the tissue cultures. Because the plants thus produced are genetically identical, the new loblolly pine '01PM0038' presents high uniformity in growth and quality. The present invention also relates to loblolly pine, and plant parts thereof, that is the loblolly pine '01PM0038'. The present invention also relates to loblolly pine, and plant parts thereof, having all of the morphological and physiological characteristics of loblolly pine '01PM0038'. The present invention also relates to plant parts, such as pollen, seeds, cones, inflorescence, needles, embryos, cuttings, seedlings, bark, wood, oil, lumber or timber produced by loblolly pine '01PM0038'. The present invention also relates to harvested products of loblolly pine '01PM0038', such as wood, oil, pulp, or paper.

The present invention relates to a method of producing a loblolly pine variety, wherein the method is somatic embryogenesis comprising the tissue culture of the loblolly pine '01PM0038'. This method may further comprise making rooted cuttings from the reproduced '01PM0038' by planting the cuttings.

The present invention also relates to a method of producing loblolly pine progeny or hybrid thereof, comprising the steps of (a) crossing loblolly pine '01PM0038', either as the female or seed parent or male or pollen parent, with a second pine variety, and (b) selecting progeny. The second pine variety may also be '01PM0038'. In addition, this method may further comprise making progeny of '01PM0038' through wind pollination, controlled pollination, or mass controlled pollination.

The present invention also relates to a method of producing loblolly pine progeny or hybrids thereof, comprising the steps of (a) crossing loblolly pine '01PM0038', as either the female or seed parent or male or pollen parent, with a second pine variety, (b) harvesting seeds produced from said cross, and (c) producing and selecting progeny from said harvested seeds. The second variety may also be '01PM0038'.

The present invention also relates to a method of producing loblolly pine progeny, comprising the steps of selfing loblolly pine '01PM0038', and (b) selecting progeny.

BRIEF DESCRIPTION OF THE PHOTOGRAPHS

The patent or application file contains four drawings executed in color. Copies of this patent or patent application publication with color drawings will be provided by the Office upon request and payment of the necessary fees.

The accompanying photographs illustrate the overall appearance of the new loblolly pine tree '01PM0038' showing the colors as true as is reasonably possible with colored reproductions of this type. Colors in the photographs may differ slightly from the color values cited in the detailed botanical description, which accurately describe the color of '01PM0038'.

DETAILED DESCRIPTION OF THE INVENTION

The present invention provides '01PM0038' as a new, distinct and stable variety of loblolly pine that is a product of a planned breeding program conducted by the inventor(s) in 2000 in Ravenel, S.C. The objective of the planned breeding program was to develop a new loblolly pine tree with vigorous growth, high biomass production for fiber or fuel use, straight stem and high resistance to fusiform rust infection that would achieve commercial maturity sooner than typical loblolly pine trees in the Southeast coastal zone of the United States.

For purposes of this application, the term "variety" is equivalent to clone, as '01PM0038' may be reproduced asexually and all resulting individuals are essentially identical genetically.

For the purposes of this application, during "mass control pollination" (MCP) a large number of female strobili are pollinated and produce seedlings (or rooted cuttings) for use in regeneration. The large scale of MCP distinguishes this process from traditional "controlled pollination" (CP), which is used to produce seed for progeny tests in order to evaluate the genetic value of the parents. Bramlett, D. L., "Genetic Gain from Mass Controlled Pollination and Topworking," *Journal of Forestry*, vol. 95 (1997) pp. 15-19. Another difference between MCP and CP is the amount of control that is used to reduce contamination. CP flowers are isolated from any outside pollen contamination and pollen is collected and processed to be nearly 100% free of contaminating pollen. In CP, the goal is that every seed has a known mother and father. The MCP process allows some contamination, so faster and less expensive techniques are used to produce large quantities of seed with the majority of seed having a known mother and a known father.

The following traits have been repeatedly observed and are determined to be unique characteristics of '01PM0038' which in combination distinguish this loblolly pine tree as a new and distinct loblolly pine variety:

1. High rust resistance;
2. Uniform, rapid growth;
3. Stem straightness;
4. Moderate branch angle.
5. Low rate of forking.

In comparison to the full-sibling family of which it is a member, '01PM0038' differs primarily in the traits listed in Table 1.

TABLE 1

| Trait | New Variety '01PM0038' | Family 'AG-373' × 'AG-76' |
| --- | --- | --- |
| Rust infection | Low | High to low |
| Growth | Uniformly rapid | Variable low to high |
| Stem straightness | Excellent | Moderate to very good |
| Wood density | Moderately high | Unknown |
| Forking | Low | Variable low to high |

Of the many commercial varieties known to the present inventor(s), the most similar in comparison to the new loblolly pine '01PM0038' is *Pinus taeda* AA-93 (unpatented), in the following characteristics described in Table 2:

TABLE 2

| Trait | New Variety '01PM0038' |
| --- | --- |
| Rust resistance | Similar to AA-93 |
| Volume Growth | Superior to AA-93 |
| Stem straightness | Similar to AA-93 |
| Wood density | Unknown |
| Branch allocation | Poorer than AA-93 |
| Forking | Similar to AA-93 |

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

EXAMPLES

Example 1

Breeding of '01PM0038'

The new *Pinus* variety is a product of a controlled breeding program conducted by the inventor(s), in Ravenel, S.C. The objective of the breeding program was to develop a new loblolly pine tree with vigorous growth, straight stem and high resistance to fusiform rust infection that would achieve commercial maturity sooner than typical trees in the Southeast coastal zone.

The new *Pinus* variety originated from a cross made by the inventor(s) in 2000 in Ravenel, S.C. The new *Pinus* variety is a progeny of a first-generation selection pollinated by a second-generation selection. The female or seed parent is the unpatented *Pinus taeda* variety AG-373 selected in Williamsburg County, South Carolina, and is a first-generation selection. The male or pollen parent is the unpatented *Pinus taeda* variety designated AG-76 selected in a progeny test in Georgetown County, South Carolina, and is a second-generation selection.

Cross pollination occurred in 2000 followed by induction of somatic embryogenesis tissue and cryopreservation of embryogenic tissue in 2001 in Summerville, S.C. The first somatic seedlings of the new *Pinus* variety were produced in 2002. Rooted cuttings were produced from the somatic seedling hedges and then planted in 2004 in 2 field experiments located in Berkeley County, South Carolina, and Randolph County, Georgia. Among these two field experiments, a total of 16 ramets of the new *Pinus* variety were planted with 8 ramets per field experiment.

The new *Pinus* variety was discovered and selected by the inventors within the progeny of the stated cross in 2010. The new *Pinus* variety was selected by the inventors based on its superior growth and resistance to fusiform rust infection, and low rates of forking and stem sinuosity.

Asexual reproduction of the new *Pinus* variety by somatic embryogenesis, a tissue culture technique for embryo multiplication, was first performed in August 2001, in Summerville, S.C., and the propagated variety has demonstrated that the combination of characteristics as herein disclosed for the new variety are firmly fixed and retained through successive generations of asexual reproduction. The new variety reproduces true to type.

Example 2

Description of '01PM0038'

The new *Pinus* '01PM0038' has not been observed under all possible environmental conditions. The phenotype of the new loblolly pine tree variety may vary with environmental variations such as temperature, light intensity and day length, as well as, growing conditions variations such as irrigation, fertilization, pruning, and pest control, without any change in the genotype of the new loblolly pine tree variety.

Figure 1:
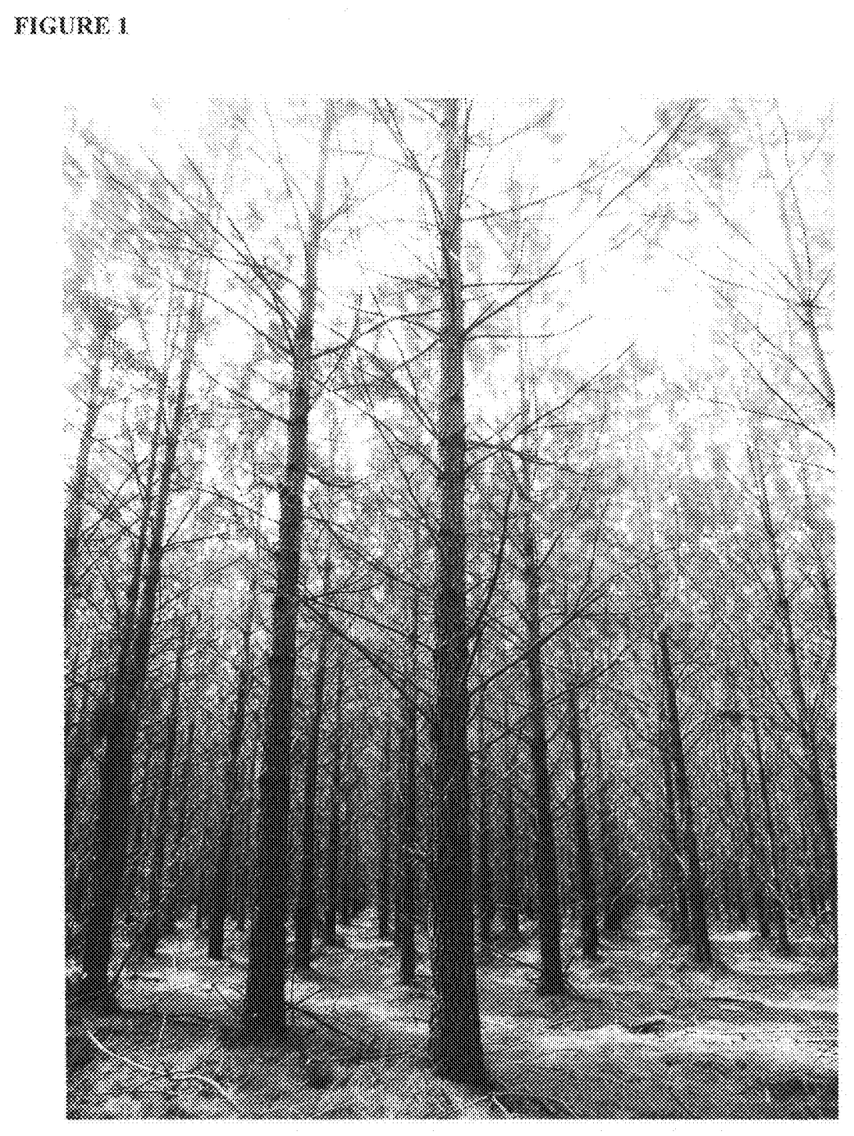
FIG. 1 shows a side perspective view of a loblolly pine tree of '01PM0038', 37 feet tall, at age 7, grown in a field experiment in Berkeley County, South Carolina.
Figure 2:
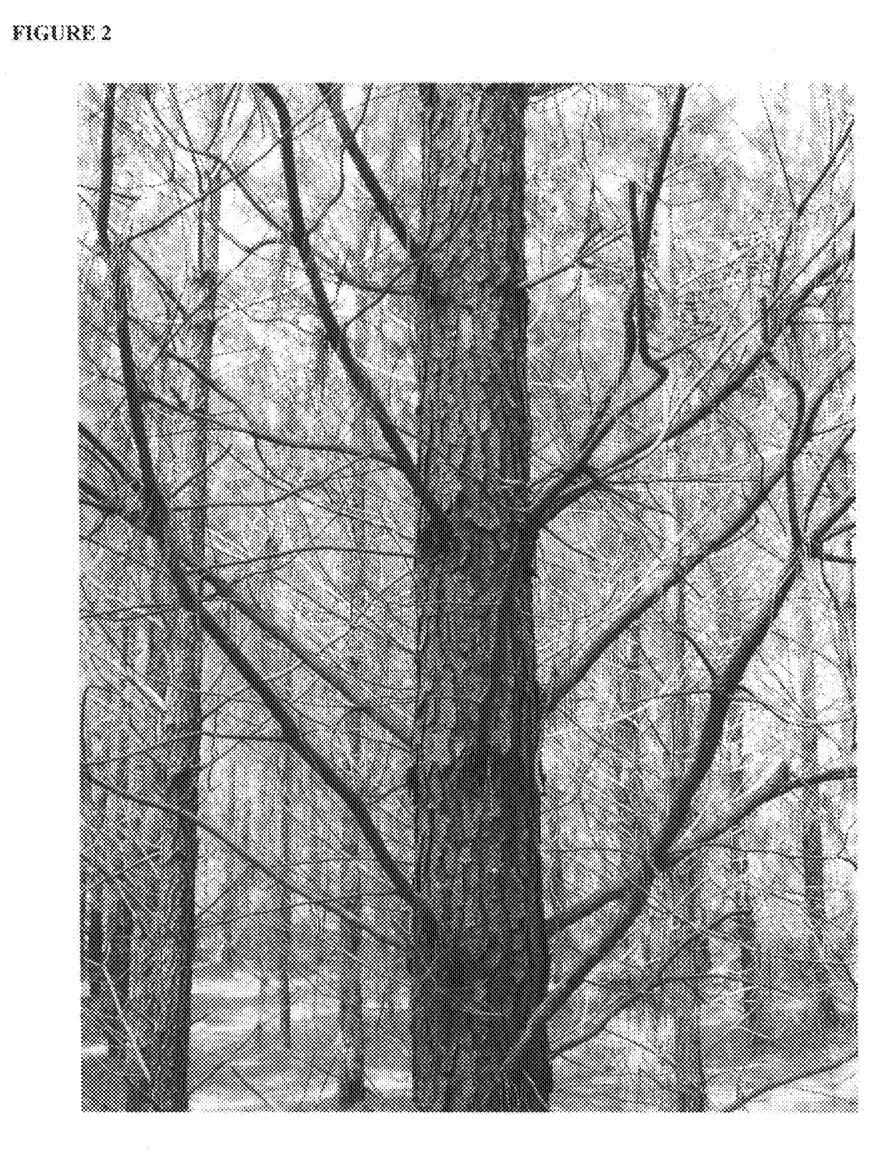
FIG. 2 shows the moderate branch angle of '01PM0038', 37 feet tall, at age 7, grown in a field experiment in Berkeley County, South Carolina.
Figure 3:
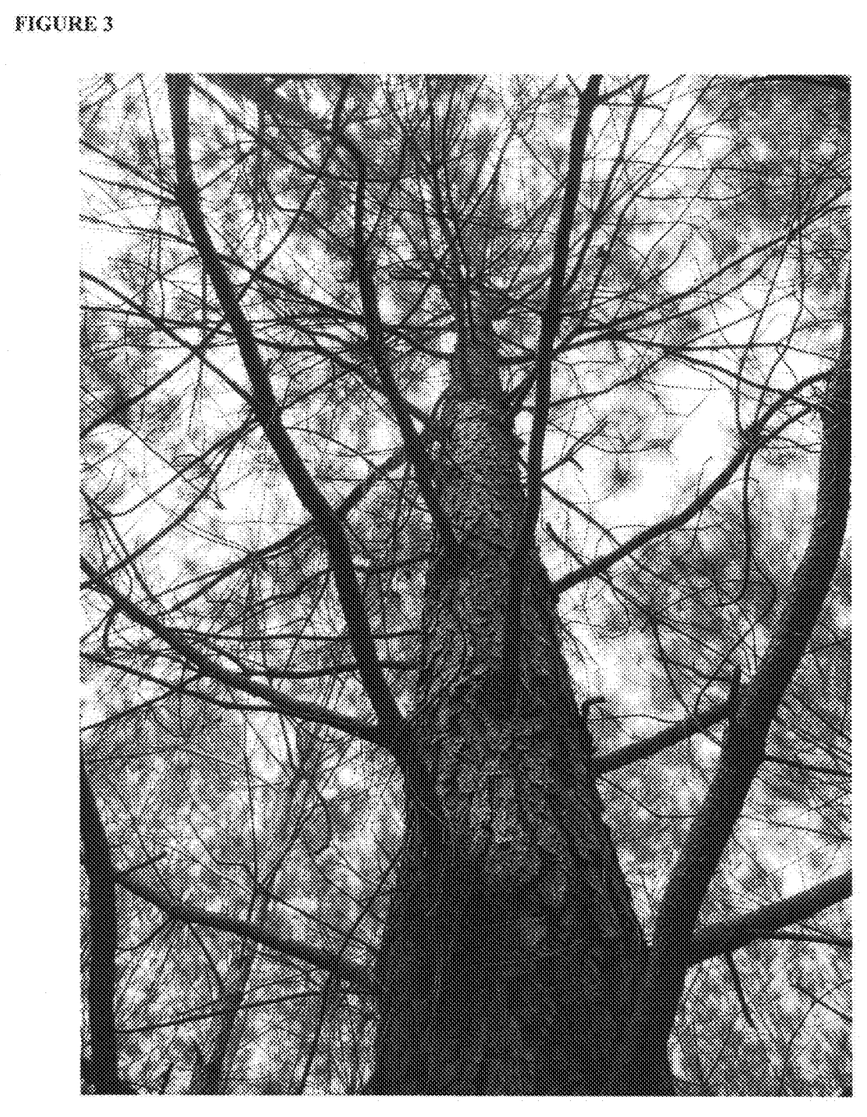
FIG. 3 shows the typically straight stem, moderate branch angle and diameter growth of '01PM0038'.
Figure 4:
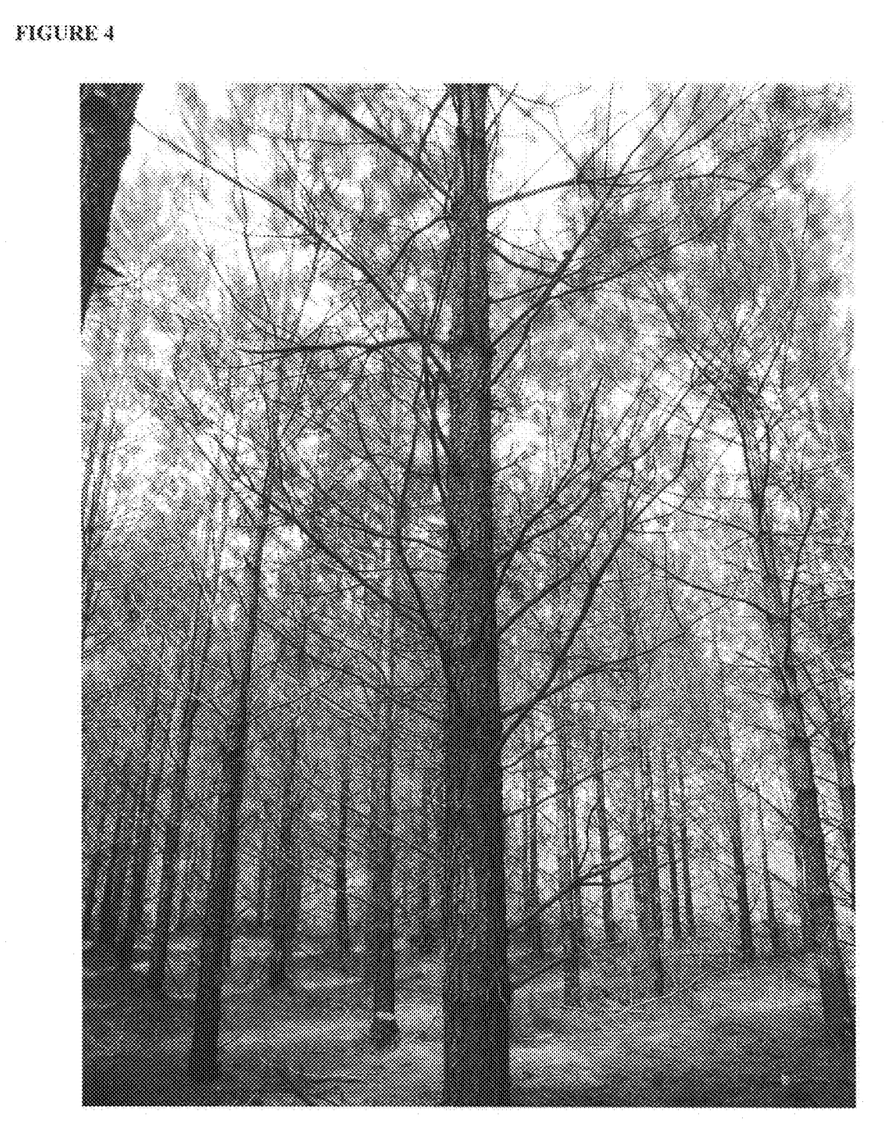
FIG. 4 shows a side perspective of the first 20 feet of '01PM0038'.

The aforementioned photographs, together with the following observations, measurements and values describe loblolly pine trees of '01PM0038' as grown in the pine farms in Berkeley County, South Carolina, and Randolph County, Georgia, under conditions which closely approximate those generally used in commercial practice.

Unless otherwise stated, the detailed botanical description includes observations, measurements and values based on 7-year old '01PM0038' trees grown in the pine farm in Berkeley County, South Carolina, from autumn of 2011 to summer of 2012. Quantified measurements are expressed as an average of measurements taken from a number of trees of '01PM0038'. The measurements of any individual tree, or any group of trees, of the new variety may vary from the stated average.

Color references are made to the MCC Munsell Color Charts For Plant Tissues (MCC), 1968 edition, except where general colors of ordinary significance are used. Color values were taken under daylight conditions at approximately 11:00 a.m. in Berkeley County, South Carolina.

All of the trees of '01PM0038', insofar as they have been observed, have been identical in all the characteristics described below.

Classification:
    Botanical: *Pinus taeda*
Parentage:
    Female or Seed Parent: *Pinus taeda* variety designated 'AG-373' (unpatented), selected in Williamsburg County, South Carolina, and is a first-generation selection.
    Male or Pollen Parent: *Pinus taeda* variety designated 'AG-76' (unpatented), selected in Georgetown County, South Carolina, and is a second-generation selection.
Propagation: Somatic embryogenesis
Growing Conditions:
    Light intensities: Full sunlight.
    Temperature: Average summer maximum temperature of 90 degrees F., and average minimum winter temperature of 36 degrees F.
    Fertilization: None.
    Growth regulators: None.
    Pruning or trimming requirements: None.
Tree:
    Age: Observed trees were 7 years old.
    Vigor: The height growth rate of '01PM0038' is $10^{th}$ among 108 loblolly pine varieties, at about 161 terminal growth per year.
    Form and Habit: A pine tree that is upright and conical in shape with whorled, moderate diameter branches that form a moderate angle to the trunk. Canopy is narrower than typical loblolly pine trees. The occurrence of rust infection is very low. A mature tree of '01PM0038' is expected to approach about 33 m in height at age 25.
    Branching habit: Whorled. Main branch angle is 40° to 45° with respect to the perpendicular to the trunk if allowed to grow naturally.
    Size (7 years old):
        Height: About 11.3 m
        Diameter: About 19.7 cm.
Roots:
    Time to initiate roots: About 4 to 6 weeks.
    Texture: Bark texture varies by age. Immature bark is scaly and mature bark is irregular blocky.
    Bark color: Primarily MCC 7.5 YR 5/2, with MCC 7.5 YR 5/4, underbark.
    Trunk Lenticels: None visible.
Primary Branches:
    Number per tree: About one set of 2-5 branches/whorl every 40 cm along trunk.
    Length: Varies due to conical shape of tree; maximum of about 250 cm; minimum of about 30 cm. On average, branches grow about 20 cm to 30 cm, and then new branchlets form, radiating from the older, primary branch.
    Diameter (at 3.5 years): About 20 mm to 25 mm
    Surface texture: Somewhat scaly and rough
    Pubescence: None.
    Color:
        Mature: MCC 7.5 YR 5/4
        New Growth: MCC 5.0 YR 5/4
Branchlets:
    Number per primary branch: About 3-4 every 15-20 cm along branch Length: Maximum of about 60 cm; minimum of about 15 cm
Diameter: About 4 mm to 10 mm
Surface texture: Smooth to rough
Pubescence: None.
Color:
   Mature: MCC 7.5 YR 5/4
   New Growth: MCC 5.0 YR 5/4
Internode length: 4 to 6 growth cycles per year. Length varies by growth condition, averaging greater than 30 cm per cycle.
Internode diameter: Varies by position on the tree. Ranges from about 15 cm at base to 1.0 cm at top.
Branch lenticels: None
Foliage:
Juvenile Needles:
   Arrangement: Single and arranged in spiral
   Duration: Produced for about 3 months to 1 year.
   Size:
      Length: About 20 mm to 40 mm
      Width: About 0.5 mm to 1.0 mm
   Shape:
      Overall: Acicular
      Apex: Acute
      Base: Sessile
   Margin: Entire
   Orientation: Lateral
   Aspect: Straight
   Texture: Glabrous
   Color:
      Upper surface: Fascicle base, MCC 7.5 GY 4/4, graduating to MCC 7.5 GY 4/4 at needle tip
      Under surface: Fascicle base, MCC 7.5 GY 4/4, graduating to MCC 7.5 GY 4/4 at needle tip
   Scale leaves: None present
Mature Needles:
   Arrangement: Evergreen needles, typically 3 needles per fascicle.
   Duration: Without injury, needles can persist for about 2 years.
   Size:
      Length (including sheath): About 120 mm to 220 mm
      Width: About 0.5 mm to 1.0 mm
   Shape:
      Overall: Acicular
      Apex: Acute
      Base: Sessile
   Margin: Entire
   Orientation: Lateral
   Aspect: Straight to somewhat twisted
   Texture: Glabrous
   Color:
      Upper surface: Fascicle base, MCC 7.5 GY 3/4 graduating to MCC 7.5 GY 3/4 at needle tip
      Under surface: Fascicle base, MCC 7.5 GY 3/4 graduating to MCC 7.5 GY 3/4 at needle tip
   Venation:
      Pattern: Linear
      Color: MCC 7.5 GY 3/4
   Sheath:
      Size:
         Length: About 10 mm to 15 mm
         Width: About 2 mm to 3 mm
      Color: MCC 7.5 YR 7/2
   Fragrance: Similar to turpentine and lemon-lime Buds:
   Type: Terminal and secondary
   Shape: Narrowly ovoid
   Length: About 5 mm to 15 mm
   Width: About 3 mm to 6 mm
   Texture: Covered with scales
   Color: Apex, MCC 5 YR 6/4, and base, MCC 5 YR 6/4
   Scales:
      Number: About 8 to 10
      Overall shape: Triangular
      Apex shape: Mucronate
      Base shape: Broadly rounded
      Color:
         Upper: MCC 2.5 YR 5/8
         Lower: MCC 2.5 YR 5/8
Cones:
Natural flowering season: February to March in Summerville, S.C.
Type: Monoecious; cone description provided for female cones.
Immature Cone (unopened):
   Overall Shape: Ovoid to cylindrical
   Length: About 75 mm to 130 mm
   Width: About 20 mm to 30 mm
   Weight: About 30 gm to 150 gm
   Texture: Irregular surface with short spine on each scale
   Color: Apex, MCC 2.5 YR 6/4, and base, MCC 2.5 YR 6/4
   Peduncle (rachis):
      Length: About 60 mm to 100 mm
      Width: About 3 mm to 6 mm
      Texture: Not visible in unopened cone, covered with scales
      Color: MCC 5 YR 4/8
   Scales:
      Number per peduncle (rachis): About 120
      Overall shape: Exposed portion (apex) loosely quadrilateral
      Apex shape: Loosely quadrilateral
      Base shape: Not visible in unopened cone
      Color: MCC 5 YR 5/4
Mature Cone (opened):
   Age: Generally by about 10 years
   Overall Shape Ovoid to narrowly conical
   Length: About 75 mm to 150 mm
   Width: About 40 mm to 60 mm
   Weight: About 10 gm to 40 gm
   Texture: Scale surfaces smooth except for short spine
   Color: Apex, MCC 2.5 Y 8/4, and base, MCC 2.5 Y 8/4
   Peduncle (rachis): Inseparable from scales that cover it
      Length: About 60 mm to 100 mm
      Width: About 3 mm to 6 mm
      Texture: Not visible, covered with scales
      Scales:
         Number per peduncle (rachis): About 120
         Type: Umbo dorsal.
         Overall shape: Rectangular, flared at apex and narrowing at base
         Apex shape: Mucronate umbo
         Base shape: Narrowing to juncture with peduncle
         Color: MCC 2.5 Y 8/4
Seeds:
   Number per scale: About 2
   Type: Anemophilous
   Overall Shape Somewhat triangular, with a raised center
   Length: About 5 mm
   Diameter: About 4 mm
   Texture: Smooth
   Color: Dark (MCC 5 YR 3/2) to light brown (MCC 7.5 YR 6/8), sometimes mottled Seed wing:
　　Attachment: Articulate
　　Length: About 20 mm
　　Width: About 8 mm
　　Color: MCC 5 YR 4/6
Use:
　　High yield industrial plantations
Disease/Pest Resistance:
　　Free of fusiform rust infection in field trees through age 7 USDA Resistance Screening Center testing, using artificial inoculation with rust spores, yielded a 5% infection rate. Control rates were between 50-88%.
Disease/Pest Susceptibility:
　　No further pest testing has been done.
Weather Hardiness/Tolerance:
　　No testing has been conducted Example 3

Genetic Fingerprinting Data of '01PM0038'

Molecular markers are widely used to assess genetic variation and relationships among and within a species (Tautz, 1989). Simple sequence repeat (SSR) markers have been useful for studying genetic relationships in loblolly pine (Liewlaksaneeyanawin, C. et al., 2004). Here, a set of 13 loblolly pine SSR markers were used to generate a unique DNA fingerprinting profile for loblolly pine genotype '01PM0038'. The SSR primer sequences used for this analysis and GenBank accession numbers are provided below.

Materials and Methods

To generate microsatellite marker fingerprints for 22 different loblolly clonal varieties: GE34, 04QN0142, 04QN0822, 04QN0969, 04QN0979, I0580652, I0792123, I1030239, I1031750, I1031813, NQ26, NQ90, ON10, PM38, PM51, PM212, PM229, PT1056, PT5992, NQ857, PT6615, and PT7207, twelve (12) highly informative markers that were easy and unambiguous to score and well spaced across the genome were selected to distinguish genotypes (Tables 3A and 3B). Two of these markers, sifg-0493 and ript-1040, were from the same linkage, although they were still almost completely independent with a genetic map distance of 41cM.

The 5' ends of all forward primers were modified with the universal m13 sequence CACGACGTTGTAAAACGAC (SEQ ID NO: 1), and the reverse primers all had the sequence GTTTCTT at the 5' end. These were used with a fluorescently labeled m13 primer of the same sequence as the 5' modification of the forward primers. Data was generated for one negative reagent control, the 12 CTAB extracted template DNA's, and three CTAB extracted DNA's of previously genotyped reference control samples of loblolly pine; B-145-L, 487NCS (=7-56), and 20-1010). The following reagents and concentrations were used in a 6 µl volume PCR reaction to amplify products: 20 ng template DNA, 5× colorless Gotag™ rxn buffer with 15 mM $MgCl_2$ dilute to 1.0×, Promega dNTPs at 66 µM each base, 0.04 µM forward primer, 0.16 reverse primer, 0.16 µM fluorescently labeled M13 primer (dye label based on product pool in table), and 1 unit hot start Taq polymerase. Thermocycling was conducted in 96-well format using PTC-200 thermocyclers with heated bonnets from MJ-research using the following parameters: 94° C. for 2 minutes, followed by 20 cycles of 94° C. for 30 seconds, 65° C. minus 0.5° C. per cycle for 30 seconds, 72° C. for 1 minute, then 25 cycles of 92° C. for 30 seconds, 55° C. for 30 seconds, and 72° C. for 1 minute thirty seconds followed by a final extension at 72° C. for 15 minutes. The products were then held at 4° C. until analyzed.

PCR products were combined and diluted in 18 mega-ohm water into 4 product pools (Tables 3A and 3B) such that one template and several markers could be analyzed in the same capillary. Two microliters of each product pool were then loaded on an ABI 3130 genetic analyzer using the default run module for a 36 cm capillary array modified by the addition of 5 minutes to the run time. An ABI LIZ600 internal size standard was used in each well at a concentration of 10 µl size standard/ml ABI HiDi formamide. Product fragments were then analyzed with GeneMapper™ 3.7 analysis software using microsatellite default settings as the analysis method.

Binning and naming of alleles were done using a scheme which allows for freedom of marker dye modification among projects to meet specific needs while still maintaining the same allele names for unifying data sets among projects. Allele names were first assigned to PCR products from each marker run with a 15-tree reference panel. Markers from these initial reference runs were labeled in one of four dye-labels, VIC, 6-FAM, NED, or PET. The allele names for a marker were based on fragment size as it appeared for whatever dye used in the reference sample runs. Any novel allele fragments in a subsequent project are named based on their relative base pair sizing within this reference frame, and subsequently become part of an additive set of named allele bins for that marker. The largest bin set for a marker is then used for all consecutive projects. Dye migration sizing differences among project runs are corrected when needed (i.e. marker A was run with 6-FAM in project 1, but VIC in project 2) for by shifting the positions of all bins in a set to the left (−) or right (+) based on dye migration difference values collected previously. Any further refinements needed due to slight run-to-run variation can also be judged by the binning of the reference controls and should be applied to all bins in a set equally. The three positive control reference samples included in PCR and sizing in this project matched previous allele calls.

SAS and Perl procedures were used to process the data and GenAlEx v. 6.1 to calculate a genetic distance (methods=codom-genotypic) matrix.

TABLE 3A

Information on 12 microsatellite markers used for the DNA fingerprinting study.

| Locus name | Dye Label | Product Pools | Linkage Group | Position LG (cM) | Size range, bps | Number Reference Alleles |
|---|---|---|---|---|---|---|
| PtRIP-0619 | 6-FAM | 3 | 6 | 28.0 | 180-250 | 16 |
| PtRIP-1040 | VIC | 1 | 2 | 53.8 | 200-240 | 13 |
| PtRIP-1077 | VIC | 2 | 4 | 5.0 | 210-300 | 8 |
| PtSIFG-0193 | NED | 1 | 11 | 1.7 | 250-270 | 3 |
| PtSIFG-0493 | NED | 2 | 2 | 12.6 | 288-332 | 6 |
| PtSIFG-0566 | 6-FAM | 2 | 1 | 25.8 | 120-150 | 4 |
| PtSIFG-0737 | PET | 2 | 10 | 110.0 | 420-480 | 11 |
| PtSIFG-1190 | NED | 3 | 9 | 75.5 | 290-340 | 3 |
| PtSIFG-4233 | 6-FAM | 1 | 7 | 57.3 | 116-160 | 14 |
| PtSIFG-4304 | VIC | 3 | 12 | 37.0 | 408-424 | 7 |
| PtTX-4114 | 6-FAM | 4 | 3 | 35.0 | 110-170 | 9 |
| SsrPt-ctg9249 | PET | 1 | 5 | 19.9 | 170-200 | 3 |

TABLE 3B

GenBank accession numbers and sequences for SSR primer pairs used in genotyping analysis of line '01PM0038'.

| Primer | Accession Number | Primer Sequence (5'-3') | Sequence Identifier |
|---|---|---|---|
| PtRIP_0619 | BV683091 | CAGCTCTCTTAATAGCCTCGGGCACATAGCAACGCTGAAGA | SEQ ID NO: 2 |
| PtRIP_1040 | BV683133 | TCAAGGAATTCATTGGAGCCTTTGGCCATATCAAACCCAT | SEQ ID NO: 3 |
| PtRIP_1077 | BV683137 | AACATTCTAGCATGCCCCACTTGTGGTGGATGTCTCTCCTC | SEQ ID NO: 4 |
| PtSIFG_0193 | BV728742 | CCCATGCATCAATTCAAGTTTGTGCGTGGATATGGAAAAA | SEQ ID NO: 5 |
| PtSIFG_0493 | BV728661 | GAGAACATCTGCCTTGAGCCCTGGCATGATGGGTTTCTCT | SEQ ID NO: 6 |
| PtSIFG_0566 | BV728755 | ACTTAGTGGGAAAGGGGGAATTCCTCAGCCAAAAGCTCTC | SEQ ID NO: 7 |
| PtSIFG_0737 | BV728669 | GCAAGGGGAATTGCTTATGAGGGATCGCATCAGCTGTAAT | SEQ ID NO: 8 |
| PtSIFG_1190 | BV728679 | CAGGTGGCTTGGATTTCATTTCATTCAAGCGTCCTGCTTA | SEQ ID NO: 9 |
| PtSIFG_4233 | BV728685 | AGGGAAACCGCGGATTATAGCCGGAATGAAGATTGCAGTT | SEQ ID NO: 10 |
| PtSIFG_4304 | BV728793 | CATGCATGTGTGGAGGAGT CTCATGTGCTTTGATCCCCT | SEQ ID NO: 11 |
| PtTX_4114 | BV728876 | ACACATGTCTTGAGGAGTTCAATTTGATCTATAACTTTCACC | SEQ ID NO: 12 |
| SsrPt_ctg9249 | BV728813 | CTGCTCCCTCAGCTCTTCC AGACGTCACTGCCATTACCC | SEQ ID NO: 13 |

Results and Discussion

All 12 markers gave excellent results for the 22 loblolly variety samples, plus the three control samples. Allelic peaks were easily binned and called using our existing marker panels and bin sets. Of the possible 12*22=156 data points (i.e., co-dominant genotypes), 155 were scored (~1.5% missing data).

All 22 variety samples provided distinct allelic profiles, with one pair of varieties (PT6615 and PT7207) showing high allele similarity.

The sample genotypes for all 12 markers and 22 varieties plus 3 control trees are provided in Table 4. Three missing data points are contained in the table for 11031750 and one missing data point is contained in 04QN0142 (denoted by a 0 at each allele). '01PM0038' can be distinguished from other pine genotypes using the primer(s): pttx-4114, ript-0619, ript-1040, ript-1077, sifg-0193, sifg-0493, sifg-0566, sifg-0737, sifg-1190, sigf-4233, sifg-4304, and SsrPt-ctg9249.

TABLE 4

Allele fingerprinting data from 22 loblolly pine genotypes using twelve primer sets

| Sample | pttx-4114 | ript-0619 | ript-1040 | ript-1077 | sifg-0193 | sifg-0493 | sifg-0566 | sifg-0737 | sifg-1190 | sifg-4233 | sifg-4304 | SsrPt-ctg9249 |
|---|---|---|---|---|---|---|---|---|---|---|---|---|
| B145L | 130140 | 213213 | 215215 | 245247 | 256256 | 314317 | 135141 | 444450 | 312312 | 122122 | 420420 | 181181 |
| 20_1010 | 130134 | 203223 | 215221 | 247247 | 256258 | 314317 | 129129 | 450462 | 312312 | 122124 | 418420 | 178178 |
| 7_56 | 136138 | 221223 | 215215 | 241247 | 256258 | 314317 | 135135 | 450456 | 312312 | 122136 | 420420 | 175175 |
| 04QN0142 | 136136 | 221221 | 215215 | 000000 | 256256 | 314317 | 129135 | 444450 | 312312 | 122122 | 420420 | 175184 |
| 04QN0822 | 136138 | 221221 | 215215 | 247247 | 256258 | 317317 | 135141 | 444450 | 312312 | 122136 | 416420 | 175175 |
| 04QN0969 | 138140 | 223223 | 215215 | 241257 | 258258 | 317317 | 135141 | 444456 | 312312 | 122122 | 416420 | 175184 |
| 04QN0979 | 136138 | 221221 | 215215 | 235247 | 256258 | 314317 | 135141 | 444450 | 312312 | 122136 | 416420 | 175175 |
| I0580652 | 136136 | 221221 | 215225 | 245247 | 256256 | 314314 | 135135 | 456462 | 312312 | 122136 | 418420 | 175178 |
| I0792123 | 136136 | 221223 | 215215 | 241243 | 258258 | 314314 | 135141 | 444450 | 303312 | 122136 | 420420 | 175178 |
| I1030239 | 132138 | 223223 | 215215 | 243247 | 258258 | 314317 | 135141 | 444456 | 303312 | 122122 | 420420 | 175175 |
| I1031750 | 134136 | 223223 | 215215 | 000000 | 000000 | 314314 | 135141 | 450450 | 303312 | 000000 | 420420 | 175178 |
| I031813 | 132136 | 221221 | 215215 | 243247 | 258258 | 314317 | 135147 | 450450 | 303312 | 122136 | 420420 | 175178 |
| PM38 | 132138 | 221221 | 215215 | 241245 | 256256 | 314317 | 135135 | 444450 | 309312 | 122136 | 420420 | 175178 |
| GE34 | 130136 | 221221 | 215215 | 247247 | 256258 | 314317 | 129135 | 444456 | 312312 | 124136 | 418420 | 175178 |
| NQ26 | 136140 | 221221 | 221221 | 235245 | 256258 | 308314 | 129135 | 444444 | 312312 | 122124 | 420420 | 175178 |
| NQ857 | 138140 | 221225 | 215225 | 241243 | 253256 | 314317 | 135135 | 450462 | 312312 | 122136 | 420420 | 175175 |
| NQ90 | 132140 | 221221 | 215215 | 235247 | 253258 | 314314 | 129135 | 444444 | 309312 | 122122 | 416420 | 178184 |
| ON10 | 136136 | 221221 | 215215 | 235247 | 256256 | 314314 | 141141 | 444456 | 309312 | 122124 | 420420 | 175178 |
| PM212 | 138140 | 221223 | 215215 | 241247 | 256256 | 308317 | 135141 | 444450 | 312312 | 122122 | 416420 | 175178 |
| PM229 | 138140 | 221223 | 215221 | 241245 | 256256 | 314317 | 135135 | 444450 | 312312 | 122136 | 420420 | 175178 |
| PM51 | 136140 | 223223 | 215215 | 247247 | 256258 | 308317 | 135141 | 444450 | 312312 | 122136 | 416420 | 175178 |
| PT1056 | 136140 | 221221 | 215215 | 247257 | 256256 | 314314 | 129141 | 444444 | 312312 | 122124 | 416420 | 175178 |
| PT5992 | 138144 | 223223 | 215215 | 241245 | 256256 | 317317 | 129135 | 444450 | 303312 | 122122 | 420420 | 175178 |
| PT6615 | 134136 | 221221 | 215225 | 241245 | 256258 | 317317 | 129135 | 444456 | 303312 | 124136 | 420420 | 175178 |
| PT7207 | 134136 | 221221 | 215225 | 241245 | 256258 | 317317 | 129135 | 444456 | 303312 | 122124 | 420420 | 175178 |

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims. All publications and patent applications mentioned in this specification are indicative of the level of skill of those in the art to which the invention pertains.

All publications and patent applications are herein incorporated by reference to the same extent as if each individual publication or patent application were specifically and individually indicated to be incorporated by reference in its entirety.

SEQUENCE LISTING

SEQ ID NO: 1: m13 sequence
CACGACGTTGTAAAACGAC

SEQ ID NO: 2: PtRIP_0619 Primer
CAGCTCTCTTAATAGCCTCGGGCACATAGCAACGCTGAAGA

SEQUENCE LISTING -continued

SEQ ID NO: 3: PtRIP_1040 Primer
TCAAGGAATTCATTGGAGCCTTTGGCCATATCAAACCCAT

SEQ ID NO: 4: PtRIP_1077 Primer
AACATTCTAGCATGCCCCACTTGTGGTGGATGTCTCTCCTC

SEQ ID NO: 5: PtSIFG_0193 Primer
CCCATGCATCAATTCAAGTTTGTGCGTGGATATGGAAAAA

SEQ ID NO: 6: PtSIFG_0493 Primer
GAGAACATCTGCCTTGAGCCCTGGCATGATGGGTTTCTCT

SEQ ID NO: 7: PtSIFG_0566 Primer
ACTTAGTGGGAAAGGGGGAATTCCTCAGCCAAAAGCTCTC

SEQ ID NO: 8: PtSIFG_0737 Primer
GCAAGGGGAATTGCTTATGAGGGATCGCATCAGCTGTAAT

SEQ ID NO: 9: PtSIFG_1190 Primer
CAGGTGGCTTGGATTTCATTTCATTCAAGCGTCCTGCTTA

SEQ ID NO: 10: PtSIFG_4233 Primer
AGGGAAACCGCGGATTATAG CCGGAATGAAGATTGCAGTT

SEQ ID NO: 11: PtSIFG_4304 Primer
CATGCATGTGTGGAGGAGT CTCATGTGCTTTGATCCCCT

SEQ ID NO: 12: PtTX_4114 Primer
ACACATGTCTTGAGGAGTTCAATTTGATCTATAACTTTCACC

SEQ ID NO: 13: SsrPt_ctg9249 Primer
CTGCTCCCTCAGCTCTTCC AGACGTCACTGCCATTACCC

What is claimed is:

1. A loblolly pine tree variety named '01PM0038', representative seeds having been deposited under ATCC designation number PTA-122333.

2. A tissue culture of the loblolly pine tree of claim 1.

3. A plant part obtained from the loblolly pine tree of claim 1.

4. A method of reproducing plants of the loblolly pine tree variety '01PM0038' from the loblolly pine tree tissue culture of claim 2 comprising the step of multiplying '01PM0038' cells of the loblolly pine tree tissue culture through somatic embryogenesis and reproducing plants of the loblolly pine tree variety '01PM0038'.

5. The method of claim 4, further comprising making rooted cuttings of the reproduced loblolly pine tree variety '01PM0038' plants and planting the rooted cuttings.

6. A method of producing loblolly pine progeny or a hybrid thereof, comprising the steps of (a) crossing loblolly pine tree variety '01PM0038', representative seeds having been deposited under ATCC designation number PTA-122333 either as the female or seed parent or as the male or pollen parent, with a second pine variety, and (b) selecting a progeny or a hybrid thereof.

7. The method according to claim 6, wherein the second pine variety is a loblolly pine tree variety '01PM0038'.

8. A method of producing a loblolly pine progeny or a hybrid thereof, comprising the steps of (a) crossing loblolly pine tree variety '01PM0038', representative seeds having been deposited under ATCC designation number PTA-122333 either as the female or seed parent or as the male or pollen parent, with a second pine variety, (b) harvesting seeds produced from said crossing, and (c) producing and selecting progeny from said harvested seeds.

9. The method according to claim 8, wherein the second pine variety is a loblolly pine tree variety '01PM0038'.

10. A method of producing a loblolly pine progeny comprising the steps of (a) selfing the loblolly pine tree variety '01PM0038' of claim 1, and (b) selecting progeny.

11. Plant graft material obtained from the loblolly pine tree of claim 1, wherein said graft material has all the morphological and physiological characteristics of said loblolly pine tree.

\* \* \* \* \*